United States Patent [19]  [11] 4,110,618
Schuman  [45] Aug. 29, 1978

[54] ADIABATIC COMPRESSION INFRARED EMISSION VAPOR DETECTOR

[75] Inventor: Mark Schuman, Arlington, Va.

[73] Assignee: American Standard Inc., New York, N.Y.

[21] Appl. No.: 462,380

[22] Filed: Jun. 8, 1965

[51] Int. Cl.² ............................................. G01N 21/26
[52] U.S. Cl. ................................................... 250/343
[58] Field of Search ............................... 73/15, 25, 26; 250/43.5, 83.3 IR, 84, 343

[56] References Cited

U.S. PATENT DOCUMENTS

| 2,806,957 | 9/1957 | McDonald | 250/43.5 |
| 3,005,097 | 10/1961 | Hummel | 250/83.3 |
| 3,222,522 | 12/1965 | Birkebak | 250/83.3 |

Primary Examiner—Verlin R. Pendegrass
Attorney, Agent, or Firm—James J. Salerno, Jr.; Robert G. Crooks

[57] ABSTRACT

Presence of a substance in a gaseous medium is detected by introducing a controlled quantity of the gaseous medium into a variable volume chamber including a cylinder having a hemispherical end wall with optically polished internal surface, and adiabatically compressing the gas by means of a piston reciprocable with the cylinder. The face of the piston opposite the hemispherical end wall of the cylinder is also of hemispherical contour. Upon adiabatic compression of the gas the temperature thereof increases to produce spectral emissions from the gaseous constituents, modulated in accordance with the recurrent variation of volume of the chamber. A detector is provided to sense any emissions occurring within the chamber at the wavelength of the substance in question.

9 Claims, 1 Drawing Figure

U.S. Patent     Aug. 29, 1978     4,110,618
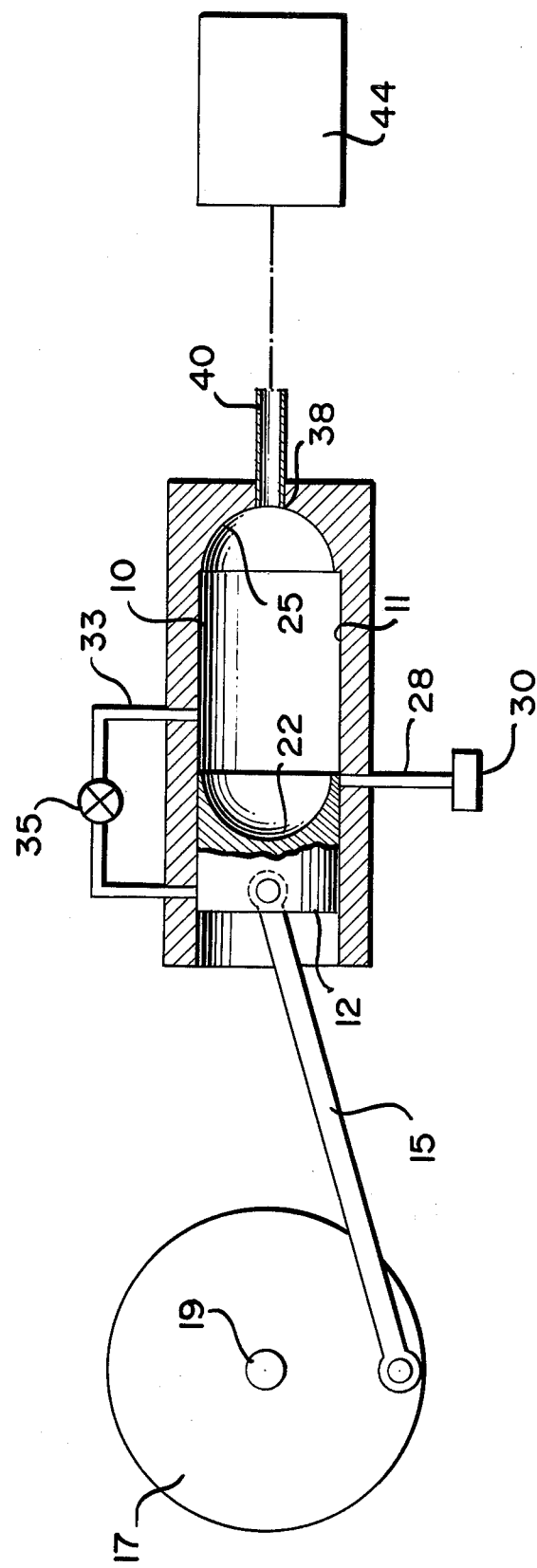

ADIABATIC COMPRESSION INFRARED EMISSION VAPOR DETECTOR

The present invention relates generally to the detection of chemical substances in gases or in mixtures of gases, the substances being in such form as vapors, agents, or aerosols in trace amounts therein, and more particularly, to the detection and measurement of such trace amounts of the substance in question by novel methods of and apparatus for examining the characteristic infrared spectral emission of such gases.

It is an object of the present invention to provide apparatus and methods for the analysis of a gaseous medium by investigation of periodic infrared spectral emissions therefrom when the medium is subjected to periodic adiabatic compression.

It is known to detect the presence of chemical agents in a gas sample, where the chemical agents have known characteristic infrared absorption, by irradiating the gas sample and a reference gas, contained in separate transparent detector chambers, with a source of infrared. If the gas sample and the reference gas absorb energy equally from the infrared passing therethrough, each will exert the same pressure on a diaphragm separating the chambers, and a condition of balance will thereby obtain. If unequal absorption occurs, the diaphragm will be displaced from its central position in accordance with the inequality of pressure existing on opposite sides thereof. By constructing the diaphragm of thin flexible conductive material, such as metallic sheet, capable of flexing upon application of relatively minute differential forces, and placing a second conductive sheet closely adjacent the metallic diaphragm, but electrically insulated therefrom, changes in capacity between the diaphragm and the sheet can be detected as these pressure differences occur. Measurements maybe made employing suitable electrical detection apparatus, such as a capacitance bridge, coupled to the diaphragm and to the plate. If the bridge is initially balanced with the unknown capacitance in one arm thereof, then any subsequent deviations in value of that unknown capacitance will result in an unbalancing of the bridge network which may readily be detected and indicated. The indication may simply be qualitative, in the form of an alarm to indicate the presence of the particular agent in question in the medium under observation, or may be quantitative, as a measurement of the amount of chemical agent present. It will, of course, be realized that a quantitative analysis of the sample gas requires that there be a linear proportionality between the magnitude of infrared absorption, the pressure or pressures exerted on the diaphragm, and the capacitance change resulting therefrom.

In a slightly different arrangement, also known, the infrared is interrupted to cause the diaphragm to vibrate at the interruption frequency, with appropriate subsequent detection.

In another known gas analyzer, of the type described immediately above, the periodic signal is obtained by providing a reciprocating diaphragm in an auxiliary chamber coupled to the transparent chamber housing the sample gas, to cause fluctuation of the quantity of absorbing gas and a corresponding variation in the vibrational amplitude of the connecting diaphragm. This arrangement dispenses with the infrared interrupter and permits the use of only one optical path, and a single infrared source.

These prior art systems are characterized by relatively long response times and high power requirements, as well as undesirable complexity and cost.

It is therefore another object of the present invention to overcome one or more of the above-mentioned disadvantages of prior art gas detectors and analyzers.

These and other objects are readily accomplished in accordance with the present invention, by the provision of apparatus comprising a variable-volume optical absorption cell in the form of a cavity, having highly reflective internal walls arranged to provide random optical paths for radiant energy reflections therein, an inlet port for introducing a sample of the gas to be analyzed into the cavity, an outlet port for exhausting the contents of the cavity, means for periodically varying the volume of the cavity to modulate the pressure and temperature of the confined gas in an adiabatic manner, thereby producing a modulated spectral radiance primarily at the characteristic absorption, and hence emission, wavelengths of the confined gas, the last-named means operating also as a valve, in conjunction with the inlet and outlet ports, to permit fractional exchange of the gas during each cycle of the periodic volume variation, and means for detecting infrared emissions at the wavelength in question. Such apparatus is useful for the detection, for example, of various contaminants, such as toxic vapors, in the air.

Also in accordance with the present invention, a process for detecting the presence of chemical agents, vapors, or aerosols, for example, having characteristic infrared emission wavelengths, in a gaseous medium such as air, comprises the steps of providing an optical absorption cell of the above-described type, introducing a controlled quantity of the gaseous medium into the cell, adiabatically compressing (and expanding) the gaseous medium in a periodic fashion to cyclically vary the temperature and pressure of the medium, and thereby to modulate the characteristic infrared spectral emission of the agent sought to be detected by the cyclic variation frequency, and filtering and measuring the alternating spectral radiant intensity within, or emanating from, the cell.

Provision is also made, in accordance with the present process, for fractional exchange of the gaseous sample under analysis at intervals corresponding to the periodic adiabatic compression and expansion.

It is, accordingly, a further object of the present invention to provide apparatus for the detection of chemical agents such as contaminants, toxic substances, particles or foreign vapors in a gas under observation by adiabatic compression-induced infrared emissions from a sample of the gas.

A still further object of the invention is to provide a process for the detection of such chemical agent and/or vapors in a gaseous medium in accordance with the observation of characteristic infrared emission of such substanced, the process involving the adiabatic compression of the gaseous sample.

To provide a better understanding of the present invention, a brief consideration of the theory underlying its development and operation is of importance at this point. Consider an optical absorption cell in the form of a cavity at temperature $T_1$, an internal surface area A, volume V, and reflectivity R, except for an area $A_d$ at which a detector sensitive to infrared absorption and having a temperature $T_1$ is disposed. Assume further that the cavity contains a gas at temperature $T_2$. If $W_1$ and $W_2$ are the blackbody radiant intensities at $T_1$ and $T_2$, respectively, in watts/cm², in the wavelength interval $\Delta\lambda$ for which the absorption coefficient of the gas is $\alpha$, then the instantaneous radiance W in the cavity is determined in the following manner.

The net emission by the gas is equal to the net absorption by the walls of the cavity plus the net absorption by the detector, or, symbolically $$(W_2 - W) 4\alpha CV = (A - A_d)(1-R)(W - W_1) + A_d(W - W_1) \quad (1)$$

or $$W = \frac{[(A-A_d)(1-R) + A_d]W_1 + 4\alpha CVW_2}{(A-A_d)(1-R) + A_d + 4\alpha CV}, \quad (2)$$

where C is the gas concentration and V is the volume of the cavity, other terms having been defined above.

Having determined the instantaneous radiance W in the cavity, the radiance $W_a$ due to the presence of the gas may readily be found by taking the difference between W and $W_1$, i.e.

$$W_a = W - W_1 = \frac{4\alpha CV(W_2 - W_1)}{(A-A_d)(1-R) + A_d + 4\alpha CV}. \quad (3)$$

The signal power S absorbed by the detector due to the gas is then simply $$S = W_a A_d = \frac{4\alpha CV(W_2 - W_1)A_d}{(A-A_d)(1-R) + A_d + 4\alpha CV} \text{ (watts)}. \quad (4)$$

Equation (4) indicates that signal power, and hence the desired detection, increases in direct proportion to the ratio of cavity volume to surface area, all other terms being held constant. A spherical cavity, with slight irregularity to enhance random radiation, is therefore the most desirable shape.

In many cases, $4\alpha CV << (A-A_d)(1-R) + A_d$ for threshold concentrations, so that $$S \approx \frac{4\alpha CV(W_2 - W_1)A_d}{(A-A_d)(1-R) + A_d}. \quad (5)$$

Consider now a compression chamber having an initial volume $V_1$ and surface area $A_1$ which may be reduced upon compression to a volume $V_2$ and surface area $A_2$. Assume further that a detector housed in a wall of the chamber covers an area $A_d$ of the chamber surface. The difference in signal power at the detector before and after compression is simply that caused by the compression of the gas under observation, so that the change in signal power absorbed by the detector is $$S \approx (W_{max} - W_1)A_d \quad (6)$$

where $W_{max}$ is radiant level in watts/cm², relative to ambient temperature, occurring at peak compression, and $W_1$ is the radiant level before compression.

Substituting equation (2) into equation (6) for $W_{max}$, with appropriate change in subscripts, $$S = \left\{ \frac{[(A_2-A_d)(1-R) + A_d]W_1 + 4\alpha qC_1{}^{V_1/q}W_2}{(A_2-A_d)(1-R) + A_d + 4\alpha qC_1{}^{V_1/q}} - W_1 \right\} A_d \quad (7)$$

where $q$ is the compression ratio $V_1/V_2$, $C_1$ is the gas concentration before compression, $q C_1$ the gas concentration after compression, and $V_2 = V_1/q$, Reducing and by analogy to development of equation (5), $$S = \frac{4\alpha C_1 V_1 (W_2 - W_1) A_d}{(A_2 - A_d)(1-R) + A_d}. \quad (8)$$

Brief consideration of equations (5) and (8) will reveal that the detectable signal power in the case of a compression chamber is greater than that in the case of a heated sphere for the same $(W_2 - W_1)$, i.e., the difference in radiant intensities at the two ambient temperatures, since that quantity is a function of the volume to area ratio in each case. In the compression chamber case the independent variables establishing this ratio are $V_1$, the volume before compression, and $A_2$, the area after compression, obviously forming a higher ratio than any V/A for the sphere case. Moreover, although the term $A_d$ has been employed as designating detector area in each case, the optimum detector for use in the compression chamber may be smaller than that which is used in conjunction with a sphere, resulting in a smaller noise equivalent power (NEP) in the former case than in the latter. Hence, signal-to-noise ratio is proportionally increased.

A suitable infrared detector for the system may comprise a temperature sensitive device, such as a thermistor bolometer having a high temperature coefficient of resistance, placed behind a spectral filter (for passing infrared at the wavelengths of interest) in the chamber wall. Such a detector is preferred because of its reliability, and system noise will therefore be calculated with reference thereto. A realistic value of detectivity for a thermistor bolometer with a flake one or two mm on a side is $$D^* = 1 \times 10^8 \sqrt{\tau} \quad (9)$$

where $\tau$ is the thermal time constant of the flake in milliseconds. Because of the specific heat and thermal conductivity of the materials on which the flake is deposited, it is relatively difficult to obtain a time constant of greater than approximately 10 ms. Selection then of, say, a time constant of 8 ms, readily obtainable in practice, results in a detectivity of, from equation (9)

$$D^* = 2.8 \times 10^{8.}$$

Hence, the noise equivalent power is $$NEP = \sqrt{A_d B}/D^*, \quad (10)$$

where B is the bandwidth under observation, and for the value of $D^*$ obtained, $$NEP = 3.57 \times 10^{-9} \sqrt{A_d B}.$$

If each of the two flakes of the thermistor is used in a bridge circuit, with each flake having the same resistance, there will be a reduction in signal by a factor of 2 and in noise by a factor of $\sqrt{2}$. In addition, for a low sinusoidal fluctuation frequency the contribution of the electronic measuring apparatus (coupled to the detector) to the system noise may be made relatively small, less than 10 percent at 10 cps. Therefore, the effective system noise, with reference to these considerations, is $$NEP = 3.57 \times 10^{-9} \sqrt{A_d B} \sqrt{2} \times 1.1 = 5.53 \times 10^{-9} \sqrt{A_d B} \text{ watts.} \quad (11)$$

The sensitivity of detection in the compression chamber is, from equations (8) and (11)

$$S/N = \frac{4\alpha C_1 V_1 (W_2 - W_1) A_d}{[(A_2 - A_d)(1-R) + A_d] 5.53 \times 10^{-9} \sqrt{A_d B}} \quad (12)$$

For sudden compression of a gas in the variable volume cavity essentially adiabatic conditions will prevail, characterized by $pV^\gamma = K_1$ and $TV^{\gamma-1} = K_2$, where $\gamma$ is the ratio of specific heat at constant pressure to the specific heat at constant volume, and $K_1$ and $K_2$ are constants. in the subsequent description of an exemplary embodiment and process in accordance with the present invention, the compression is at adiabatic or substantially adiabatic conditions.

In a typical portable field unit, initial temperature was 27° C., compression temperature 190° C., modulation frequency (reciprocation rate) 10 cps, compression ratio 4/1, maximum pressure (gauge) 5 atm., initial volume 2.57 cm³, maximum force on piston 10 lb., total power requirement (furnished by nickel-cadmium batteries) 5.9 watts, operating time 12 hours, detector size 1.5 mm × 1.5 mm. These values are to be taken as illustrative only; others are quite feasible.

Having briefly described the present invention and having set forth some of the principles underlying its operation, the above and still further objects, features and attendant advantages of the invention will become apparent from a consideration of the following detailed description of a specific embodiment thereof, especially when taken in conjunction with the accompanying drawing in which:

The sole FIGURE illustrates an exemplary embodiment of an optical compression chamber and detection system in accordance with the present invention.

Referring now to the drawing, an optical absorption cell includes a chamber 10, alternatively termed a cavity, having a generally cylindrical internal wall surface 11 and an open end adapted to receive a piston 12. The piston is dimensioned to slide freely internally of the chamber while maintaining a relatively close fit or tolerance between its outer surface and the internal wall surface 11 of the chamber.

To produce the desired reciprocation of piston 12 from an internal position adjacent the open end of chamber 10 to a position adjacent the closed end, a connecting rod 15 is pivotally fastened, in any conventional manner, at one end to a rotating flywheel 17 driven via shaft 19 by a suitable motor (not shown), and at the other end to the bottom of the piston.

The top face 22 of the piston and top surface 25 of the chamber each have an approximately hemispherical shape so that at maximum compression the optical cavity becomes substantially spherical. The surfaces of the cavity, i.e., the internal wall surface 11 and top surface 25 of the chamber and face 22 of the piston, are optically polished for high reflectivity so that large amplitude spectral radiance will occur during the process.

An air, or other gas, sample inlet port is provided in the form of intake pipe 28 and filter 30. Similarly, an outlet port is provided by pipe or duct 33, the interior of which is exposed at the internal wall surface of the chamber 10, and having a variable exhaust valve 35 disposed along the path of the exhaust line to permit adjustment of the quantity of gas to be exhausted from the chamber during each cycle of reciprocation of piston 12.

A detector 40, such as a thermistor bolometer, located immediately behind a spectral filter 38 in the wall of cavity 10, as previously discussed, is employed to sense the characteristic infrared spectral emission of the chemical agents or vapors under observation. Such sensing will, of course, occur only if the particular chemical agent or vapor in question is present in the gas sample contained within the cavity.

Suitable electronic measuring apparatus 44 including, for example, a bridge circuit and synchronous rectifier along with an alarm and/or a meter (not shown) to indicate the presence and/or amount, respectively, of the substance of interest in the gas sample, may be coupled to the detector.

In operation of the system, the air or other gas introduced into the chamber undergoes adiabatic compression, with a concurrent increase in the temperature of the gas sample, as piston 12 moves inwardly of the chamber 10 under the control of the connecting rod 15, flywheel 17, shaft 19 and suitable driving means (not shown). Any trace amounts of the substance of interest which may be present in the gas sample under observation will emit radiant energy at its characteristic infrared wavelength as a result of the increase in temperature of the sample. Filter 38 may be made readily replaceable or selectively adjustable to permit observation by detector 40 of only the infrared spectral emission of interest and to permit the use of the same apparatus to determine the presence of a variety of agents, gases or vapors within a gaseous sample.

Moreover, the thermal decomposition or chemical reaction of the specific agents at high temperatures and pressures may be used as a method of enhancing the detection of such agents by the apparatus and operation described. It is notable that the power consumption of the device illustrated in the drawing is relatively low because much of the energy of compression is returned to piston 12 as the latter moves outwardly of the cavity.

The air intake 28 in conjunction with the operation of pistor 12 functions as a vavle to supply gas to be analyzed to the cavity in an amount sufficient to prevent equalization of pressure inside and outside the cavity (i.e., both equaling atmospheric pressure). Equalization otherwise gradually occurs with leakage of the sample gas about the piston. Such loss of air might cause a reduction in the peak to peak temperature, with cyclic movement of the piston, sufficient to cause substantial reduction in signal power. The gas sample inlet is arranged to be uncovered or exposed by the passage of the piston as the piston reaches the bottom of its stroke, i.e., a position adjacent the open end of the chamber, so that the minimum pressure of the gas within the chamber is at atmospheric to maintain an easily detectable signal level. The gas leakage itself may be reduced to a greater extent by the use of sealing rings, such as O-rings or other piston rings.

Both ends of the exhaust tube or pipe are open only during a small portion of the cycle, as will readily be observed by reference to the illustrated width of the piston relative to the distance between exhaust inlet and outlet, at an interval during which the pressure of the gas sample is slightly above atmospheric so that the power loss is reduced over that which would occur if air were exhausted from the chamber at high pressures. Flow of the gaseous sample into the chamber 10 through gas intake and filter 28 and 30, respectively, and out of the chamber around the piston via exhaust line 33 guarantees a finite response time as well as a selectable one, to the sudden presence of the chemical agent of interest. If necessary, or desirable, the response time may be decreased or increased by adjustment of variable exhaust valve 35 in exhaust line 33.

Compression for signal purposes begins with the closure of the more inward exhaust port by the piston during the up stroke. The compression ratio may be calculated from this point. Hence, the small portion of the stroke at the exhaust portion of the cycle is merely to permit the transfer of sample gas into the chamber.

The above detailed description will reveal that the present invention permits reduction in size and in power loss over prior art detectors, and, in addition, may be embodied in a relatively simple, yet rugged, construction to provide increased sensitivity and response time and decreased size, weight and cost.

While I have illustrated and described one specific embodiment of my invention, it will be apparent to those skilled in the art from a consideration of the preceding description that various changes and modifications in the specific details of construction and operation so illustrated and described may be resorted to without departure from the spirit and scope of the invention. It is therefore desired that the present invention be limited only by the appended claims.

I claim:

1. Apparatus for the detection of contaminants in a gaseous medium by observation of the characteristic infrared spectral emissions of said contaminants, comprising a variable volume opaque optical cavity of at least partly spherical shape and having highly reflective walls, means for varying the volume of said cavity for periodic adiabatic compression of a sample of said gaseous medium within said cavity, whereby the temperature of said sample varies in accordance with $TV^{\gamma-1} = K$, where $T$ is the temperature, $V$ the volume, and $\gamma$ the ratio of specific heats at constant pressure and constant volume for said sample, and K is a constant, said emissions occurring upon increase in temperature of said sample concurrent with compression thereof if said contaminants are present therein, said highly reflective walls and at least partly spherical shape of said cavity providing random optical paths for said emissions and high amplitude spectral radiance, and means responsive to said emissions for absorbing infrared therefrom to detect the presence of said contaminants, or any one of them, in said sample.

2. The combination according to claim 1 further including means coupled to said means for absorbing for measuring the quantity of said contaminants, or any one of them, present in said sample.

3. Apparatus for the detection and measurement of chemical agents in a gaseous medium by observation of characteristic infrared spectral emissions therefrom, comprising a variable volume optical cavity, said optical cavity having highly reflective surfaces arranged to provide random optical paths for said emissions, means for cyclically varying the volume of said cavity for compression and expansion of a sample of said gaseous medium within said cavity in an adiabatic fashion, so that the increase in temperature of said sample during said compression resulting in said emissions is related in a uniform manner to the decrease in volume of said cavity, said emissions occurring if said agents or any one of them are present in said sample, and means responsive to said emissions for absorbing infrared therefrom to detect the presence of one or more of said agents in said sample.

4. The combination according to claim 3 wherein said variable volume optical cavity comprises a chamber having optically polished internal surfaces and a piston having an optically polished face, said piston arranged to cooperate with said chamber in periodic motion inwardly and outwardly thereof, and to form with said chamber a substantially sperical cavity at maximum compression of said sample.

5. Apparatus for detection of chemical agents or vapors in a gaseous medium by observation of the characteristic infrared spectral emissions of said agents or vapors, comprising a variable volume optical cavity, said cavity having highly reflective walls and a hemispherical contour, means for periodically varying the volume of said cavity in an adiabatic process to cyclically compress said sample, whereby the temperature of said sample is increased during said compression in a fixed relationship with the volume of said cavity, the increase in temperature of said sample producing said emissions from said agents or vapors if present therein, means for exchanging at least a fraction of the gaseous medium within said cavity with a similar fraction taken from a source of said medium during each periodic variation in the volume of said cavity, thereby to provide a new sample of said gaseous medium for observation, and means responsive to same emissions for absorbing infrared therefrom to indicate the presence of said agents or vapors in the particular sample of said gaseous medium under observation.

6. The combination according to claim 5 wherein said means for exchanging includes means for introducing a predetermined quantity of said gaseous medium into said cavity during each period of said variation in cavity volume, and for exhausting a predetermined amount of the sample of said gaseous medium within said cavity during a corresponding period, and further includes said means for periodically varying.

7. Apparatus for analyzing a gas or mixture of gases to detect the presence of given aerosol or gaseous matter therein through characteristic infrared emission by said matter upon increase in temperature of said gas, said apparatus comprising a chamber, said chamber including a cylinder having a partially spherical end wall with polished internal surface, means for permitting the passage of said gas through said chamber, means including a piston arranged to reciprocate within said cylinder for periodically varying the pressure of said gas within said chamber in adiabatic fashion to vary the temperature of said gas in predetermined relationship therewith, said piston having an optically polished face of partly spherical contour opposite said end wall of said cylinder, and infrared detection means selectively responsive to said emission by said matter to indicate the presence thereof within the gas or gas mixture in said chamber.

8. The combination according to claim 7 wherein said infrared detection means comprises means for selectively filtering said characteristic infrared emission, and means for absorbing energy from the filtered emission.

9. The combination according to claim 7 further including means coupled to said infrared detection means for the quantative measurement of said given aerosol or gaseous matter present within the gas or gas mixture in said chamber.

* * * * *